(12) United States Patent
Kim et al.

(10) Patent No.: US 8,187,443 B2
(45) Date of Patent: May 29, 2012

(54) APPARATUS FOR SEPARATING CELL USING CENTRIFUGAL FORCE AND DIELECTROPHORESIS

(75) Inventors: Byungkyu Kim, Gyeonggi-do (KR); Jaemin An, Gyeonggi-do (KR); Sang-Mo Shin, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 168 days.

(21) Appl. No.: 12/810,321

(22) PCT Filed: Dec. 24, 2008

(86) PCT No.: PCT/KR2008/007659
§ 371 (c)(1),
(2), (4) Date: Jun. 24, 2010

(87) PCT Pub. No.: WO2009/084858
PCT Pub. Date: Jul. 9, 2009

(65) Prior Publication Data
US 2010/0282611 A1    Nov. 11, 2010

(30) Foreign Application Priority Data
Dec. 28, 2007  (KR) .................. 10-2007-0140691

(51) Int. Cl.
*G01N 27/447* (2006.01)
(52) U.S. Cl. ...................................... 204/643
(58) Field of Classification Search .......... 204/600–621, 204/641–645; 435/287.2, 7.1, 6; 436/177
See application file for complete search history.

(56) References Cited

U.S. PATENT DOCUMENTS
2004/0126254 A1*  7/2004  Chen et al. ................. 417/423.1

FOREIGN PATENT DOCUMENTS
| JP | 2003-066004 A | 3/2003 |
| JP | 2004-361198 A | 12/2004 |
| KR | 10-2006-0018474 A | 3/2006 |
| KR | 10-2006-0068979 A | 6/2006 |

OTHER PUBLICATIONS

Patent Abstracts of Japan, Publication No. 2003-066004, dated Mar. 5, 2003, 1 page.
Patent Abstracts of Japan, Publication No. 2004-361198, dated Dec. 24, 2004, 1 page.

(Continued)

*Primary Examiner* — Alex Noguerola
*Assistant Examiner* — Gurpreet Kaur
(74) *Attorney, Agent, or Firm* — Osha • Liang LLP

(57) ABSTRACT

A cell separating apparatus that can easily separate target cells contained in a fluid is provided. Target cells and a fluid are injected through a storage hole, and ejected to the outside of a rotation disk under the influence of a centrifugal force of the rotation disk. An electric field is applied to the outside of the rotation disk, and the target cells are gathered at a different position from the fluid due to di-electrophoresis. In addition, pivot arms placed at an outer surface of the rotation disk are open, and the open pivot arms collect the target cells. The collected target cell flow in a different storage portion through a fluid flow path. As a result, the target cells can be easily separated.

12 Claims, 2 Drawing Sheets

OTHER PUBLICATIONS

Korean Patent Abstracts, Publication No. 10-2006-0018474, dated Mar. 2, 2006, 1 page.
Korean Patent Abstracts, Publication No. 10-2006-0068979, dated Jun. 21, 2006, 1 page.
International Search Report issued in PCT/KR2008/007659, mailed on Aug. 3, 2009, 3 pages.
Written Opinion issued in PCT/KR2008/007659, mailed on Aug. 3, 2009, 3 pages.

* cited by examiner

[Fig. 1]
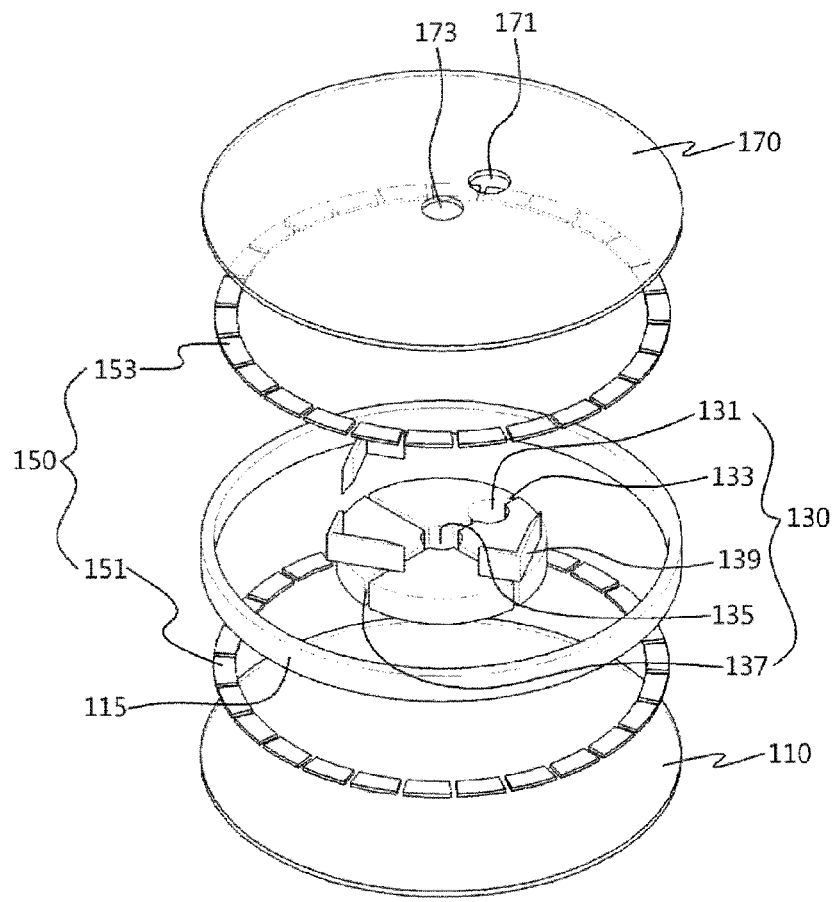
[Fig. 2]
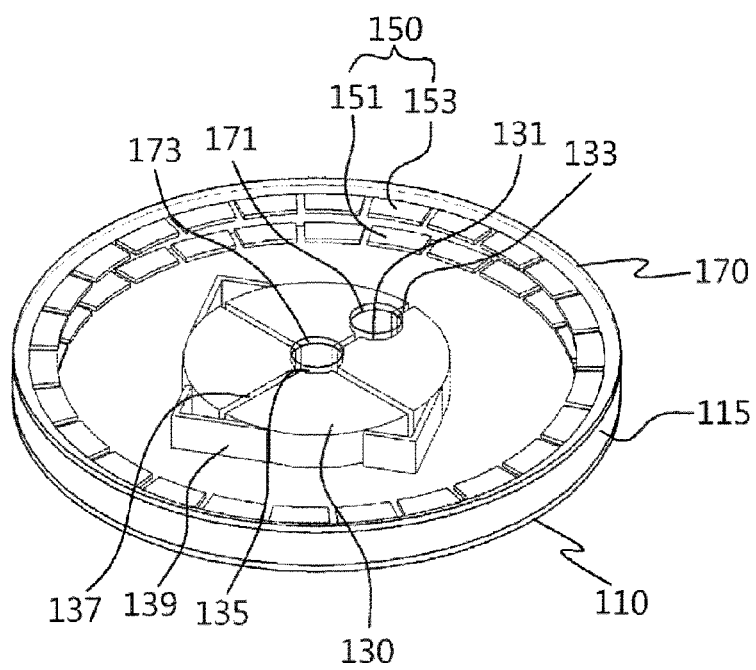

[Fig. 3]
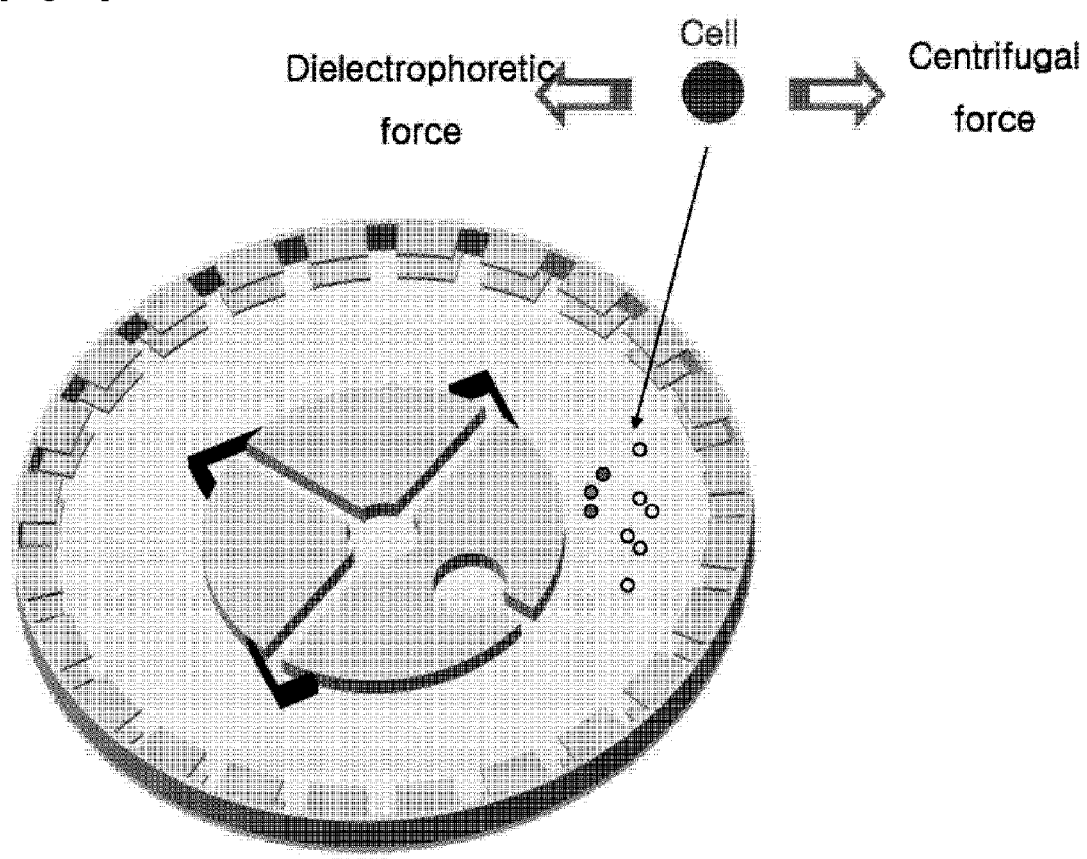

APPARATUS FOR SEPARATING CELL USING CENTRIFUGAL FORCE AND DIELECTROPHORESIS

TECHNICAL FIELD

The present invention relates to an apparatus for separating a cell using a centrifugal force and dielectrophoresis, and more particularly, to an apparatus for separating a desired cell by inducing dielectrophoresis through by a rotation disk generating a centrifugal force and electrodes spaced a predetermined distance apart from each other over and under the rotation disk.

BACKGROUND ART

Sorting of target cells is essential in current medical applications such as germ detection, development of new drugs, doping tests and cell replacement therapy. Generally, in order to separate a cell, an apparatus for sorting a target cell using a fluorescent material, such as a fluorescence-activated cell sorter (FACS), has been used. A conventional apparatus for separating a cell such as this essentially needs a pretreatment for labeling only a target cell to screen.

However, an apparatus for separating a cell using dielectrophoresis is operated based on a difference in cell's own characteristics such as conductivity and permittivity without the pretreatment. For this reason, research on separating a fine particle or a cell using dielectrophoresis has been actively conducted by many research groups.

DISCLOSURE OF INVENTION

Technical Problem

In the conventional apparatus for separating cells/fine particles using dielectrophoresis based on the micro-electromechanical systems (MEMS) technology, the cells or fine particles are generally separated due to interaction of a force generated when a fluid flows into a microchannel due to a micro-pump with a dielectrophoretic force induced by electrodes placed in the microchannel. However, in this method, since cells also flow into the microchannel through a single or limited number of inlets by the pump, throughput is limited, though it is still higher than that by the FACS.

Technical Solution

The present invention is directed to an apparatus capable of facilitating separation of a target cell using a centrifugal force and dielectrophoresis.

According to an embodiment of the present invention, an apparatus for separating a cell includes: a lower plate; a rotation disk placed on the lower plate, ejecting target cells due to a centrifugal force, and injecting the target cells aligned due to dielectrophoresis inside; an upper cover placed over the rotation disk, and accommodating the rotation disk; and microelectrode parts placed over and under the rotation disk, and forming an electric field to induce movement of the target cell due to dielectrophoresis.

Advantageous Effects

According to the present invention, the target cells can be easily separated using the centrifugal force and dielectrophoresis.

BRIEF DESCRIPTION OF DRAWINGS

These and/or other objects, aspects and advantages of the invention will become apparent and more readily appreciated from the following description of the exemplary embodiments, taken in conjunction with the accompanying drawings of which:

FIG. 1 is an exploded perspective view of an apparatus for separating a cell using a centrifugal force and dielectrophoresis according to an exemplary embodiment of the present invention;

FIG. 2 is a perspective view of the apparatus for separating a cell according to an exemplary embodiment of the present invention; and FIG. 3 schematically illustrates an equilibrium state of a target cell relocated inside the apparatus for separating a cell of FIG. 2.

BEST MODE FOR CARRYING OUT THE INVENTION

Reference will now be made in detail to the present embodiments of the present invention, examples of which are shown in the accompanying drawings.

However, it should be understood that the present invention is not limited to specific embodiments, but includes modifications, equivalents and alternatives, without departing from the spirit and scope thereof.

Here, terms "first" and "second" can be used to explain various elements, which however does not limited to these terms. The terms are only used to distinguish one element from another.

Hereinafter, exemplary embodiments of the present invention will be described in more detail with reference to the accompanying drawings. When the same element appears in different drawings, it will always be denoted by the same reference numeral and will be described only once. It should be clear that these embodiments are provided only to explain the present invention, and not to limit the scope thereof.

FIG. 1 is an exploded perspective view of an apparatus for separating a cell using a centrifugal force and dielectrophoresis according to an exemplary embodiment of the present invention.

Referring to FIG. 1, the apparatus for separating a cell using a centrifugal force and dielectrophoresis includes a lower plate 110, a rotation disk 130, microelectrode parts 150, and an upper cover 170.

The lower plate 110 supports the rotation disk 130 to allow the rotation disk 130 to be rotated by a separate rotation means. Depending on the type of embodiment, the lower plate 110 may be integrated with the rotation disk 130 to be rotated together. The lower plate 110 may be formed of a chemically-stable material, and preferably glass in a round shape.

A side cover 115 is provided along an outer surface of the lower plate 110. The side cover 115 is provided to prevent leakage of target cells and a fluid applied on the lower plate 110 to the outside. In addition, the side cover 115 is formed to almost correspond to an outer circumferential edge of the lower plate 110.

The rotation disk 130 is provided on the lower plate 110. The rotation disk 130 includes a first storage portion 131, a second storage portion 135, a first fluid flow path 133, second fluid flow paths 137 and pivot arms 139.

The first storage portion 131 is placed slightly apart from a center of the rotation disk 130. Thus, the target cells and fluid injected initially into the first storage portion 131 are affected by a centrifugal force generated when the rotation disk 130 is rotated. In addition, the first fluid flow path 133 is placed between the first storage portion 131 and the outer circumferential edge of the rotation disk 130. The target cells and fluid affected by the centrifugal force due to the rotation of the rotation disk 130 may be ejected outside the rotation disk 130 through the first fluid flow path 133.

The second storage portion 135 is formed approximately at the center of the rotation disk 130. In addition, the second fluid flow paths 137 are placed between the outer circumferential edge of the rotation disk 130 and the second storage portion 135. The target cells injected into the second fluid flow paths 137 are injected into the second storage portion 135 through the second fluid flow paths 137.

Here, the pivot arms 139 function to selectively open and close the second fluid flow paths 137 and collect target cells relocated outside of the rotation disk 130. That is, during the rotation of the rotation disk 130, the pivot arms 139 pivot in an outer direction of a radius of the rotation disk 130 to open the second fluid flow paths 137, and collect the target cells at the outside of the rotation disk 130 such that the target cells are input into the second fluid flow paths 137. Afterwards, when the rotation of the rotation disk 130 becomes slow or stops, the pivot arms 139 come back to initial positions to close the second fluid flow paths 137.

Specifically, the pivot arms 139 are placed outside the second fluid flow paths 137, and formed in approximately a "⌐" shape. One end of each of the pivot arms 139 is coupled to the rotation disk 130, whereas the other end thereof is not physically coupled to the rotation disk 130. Accordingly, when the rotation of the rotation disk 130 becomes slow or stops, the pivot arms 139 block the second fluid flow paths 137 from the outside. However, when the rotation disk 130 has a predetermined torque, the end that is not coupled to the outer surface of the rotation disk 130 may be affected by a centrifugal force. Alternatively, when the rotation disk 130 is rotated, fluid resistance may be generated from the outer circumferential surface of the rotation disk 130 to a projecting portion of the pivot arms 139. According to action of the resistance, the pivot arms 139 pivot, and thus open the second fluid flow paths 137. The pivot arms 139 opening the second fluid flow paths 137 rotate, thereby collecting target cells aligned in a direction of the rotation disk 130. The collected target cells are injected into the second storage portion 135 through the second fluid flow paths 137.

The microelectrode parts 150 are placed over and under the rotation disk 130. That is, the microelectrode parts 150 include first microelectrodes 151 placed under the rotation disk 130, and second microelectrodes 153 placed over the rotation disk 130. In addition, the first and second microelectrodes 151 and 153 are placed in an approximately round shape along edges of the lower plate 110 and the upper cover 170. Here, it is preferable that the microelectrodes 151 and 153 do not overlap but are adjacent to the side cover 115.

In addition, the first microelectrodes 151 may be integrated with the lower plate 110, and the second microelectrodes 153 may be integrated with the upper cover 170.

The upper cover 170 covers the top of the rotation disk 130. In addition, the upper cover 170 includes two holes corresponding to the first and second storage portions 131 and 135 of the rotation disk 130. Through these holes, the target cells and fluid may be injected or ejected. That is, the upper cover 170 has a first storage hole 171 and a second storage hole 173. Through the first storage hole 171, the target cells and fluid are injected. In addition, through the second storage hole 173, the target cells stored in the second storage portion 135 may be ejected.

FIG. 2 is a perspective view of the apparatus for separating a cell according to an exemplary embodiment of the present invention, and FIG. 3 schematically illustrates an equilibrium state of a target cell relocated inside the apparatus for separating a cell. Hereinafter, the operation of the apparatus for separating a cell will be described with reference to FIGS. 2 and 3.

The rotation disk 130 may include a rotation means (not illustrated). When the rotation disk 130 is rotated by the rotation means, a centrifugal force is generated. Due to the centrifugal force, the fluid containing the target cells stored in the first storage portion 131 flows in a direction of circumference of the rotation disk 130 through the first fluid flow path 133.

The target cells and fluid flow to the outside of the rotation disk 130 through the first fluid flow path 133 from the first storage portion 131. The first storage portion 131 is formed on the rotation disk 130, but preferably spaced a predetermined distance apart from the center of the rotation disk 130. The first storage portion 131 may be installed in plural numbers, and the plurality of first storage portions 131 may be aligned on the circumference of the same radius.

Aside from the rotation of the rotation disk 130, an electric field is formed between the first and second microelectrodes 151 and 153 due to application of a voltage. The strength of the electric field formed between the first and second microelectrodes 151 and 153 is strong in a region between the microelectrodes 151 and 153, and becomes weaker toward the center of the rotation disk 130 from the microelectrodes 151 and 153. Due to the electric field formed between the microelectrodes 151 and 153, the target cells and fluid undergo dielectrophoresis.

The term "dielectrophoresis" is a phenomenon in which when particles are less polarized than a surrounding medium, dipoles are aligned to a region of a low-density electric field, and thus the particles also move to this region. The target cells move to a center of a circle due to application of the electric field formed at the microelectrode parts 150.

If a target cell is formed in a homogeneous spherical shape, a dielectrophoretic force acting on the corresponding cell is given by:

$$F_{DEP} = 2\pi r^3 \in_m \text{Re}[K(\omega)] \nabla E^2 \quad \text{[Formula 1]}$$

where r is the radius of a particle, $\in_m$ is permittivity of a surrounding medium, $\nabla$ is a del vector operator, E is the magnitude of an electric field, and $\text{Re}[K(\omega)]$ is a real part of the Clausius-Mossotti factor, which is given by:

$$K(\omega) = \frac{\varepsilon_p^* - \varepsilon_m^*}{\varepsilon_p^* + 2\varepsilon_m^*}, \quad \text{[Formula 2]}$$

where $\in_m^*$ is complex permittivity of a medium, $\in_p^*$ is complex permittivity of a particle, and the complex permittivity is given by:

$$\varepsilon^* = \varepsilon - j\frac{\sigma}{\omega}, \quad \text{[Formula 3]}$$

where σ is conductivity, $\in$ is permittivity, and ω is the frequency of applied electric field.

Referring to Formula 1, since $\text{Re}[K(\omega)]$ is dependant on the frequency of the applied electric field, the strength of the dielectrophoretic force may also be dependant on the frequency. In addition, the value of $\text{Re}[K(\omega)]$ varies when particles are more or less polarized than the surrounding medium. That is, when particles are more polarized than the surrounding medium, Re[K(ω)] has a positive value, and in this case, the particles move to a higher electric field.

On the other hand, when the particles are less polarized than the surrounding medium, that is, Re[K(ω)] has a negative value, the particles move to a lower electric field. Thus, the less-polarized target cells are aligned in a lower electric field direction, and the more-polarized fluid is aligned in a higher electric field direction. That is, the target cells are adjacent to the rotation disk 130, and the fluid is spaced a relatively long distance apart from the rotation disk 130.

Accordingly, as illustrated in FIG. 3, the target cells and fluid are affected by both the centrifugal force acting in an outer direction of the radius of rotation and the dielectrophoretic force acting in an inner direction of the radius of rotation. That is, the target cells are positioned at a constant radius in which both the centrifugal force and the dielectrophoretic force are in equilibrium according to the characteristics of the cells.

The pivot arms 139 open the second fluid flow paths 137 due to the centrifugal force or fluid resistance induced by rotation of the rotation disk 130. The pivot arms 139 fixed to the rotation disk 130 at one ends collect the target cells adjacent to the rotation disk 130. Accordingly, the target cells can be more effectively injected into the second fluid flow paths 137. The target cells injected into the second fluid flow paths 137 are stored in the second storage portion 135.

As a result, the target cells can be effectively separated from the fluid using the centrifugal force and dielectrophoresis.

The rotation disk 130 may be fabricated by a conventional MEMS process. However, it is preferable that the pivot arms 139 are separately attached to an outer surface of the rotation disk 130 previously fabricated.

For example, in order to fabricate the rotation disk, SU-8 (Micro Chem. Corp.) is applied to a thickness of 100 μm onto a disk using a spin coater, and then patterned to form the first storage portion 131, the second storage portion 135, the first fluid flow path 133 and the second fluid flow paths 137 in a channel shape using UV. Afterwards, unnecessary parts are removed using an SU-8 developer.

The lower plate 110, the first microelectrodes 151 and the rotation disk 130 may also be fabricated by an integrated MEMS process.

That is, the first microelectrodes 151 are first formed on the lower plate 110, and the rotation disk 130 is formed on the lower plate 110 where the first microelectrodes 151 are formed.

In order to form the first microelectrodes 151, chromium, gold or an alloy thereof is deposited on the lower plate 110. Subsequently, photoresist is applied onto the deposited metal layer, and exposed to form a photoresist pattern corresponding to the first microelectrodes 151.

The first microelectrodes 151 are formed by an etching process using the photoresist pattern as an etch mask. Subsequently, the photoresist pattern is removed.

After that, the rotation disk 130 having the first storage portion 131, the first fluid flow path 133, the second storage portion 135 and the second fluid flow paths 137 may be formed by applying SU-8 onto the lower plate 110 where the first microelectrodes 151 are formed using a spin coating process, and then irradiating UV.

It will be clearly understood by those skilled in the art that the upper cover 170 and the second microelectrodes 153 may be formed in the same manners as the lower plate 110 and the first microelectrodes 151.

The apparatus for separating a cell may be easily fabricated for each component using the MEMS process as described above. The components may also be fabricated in an integrated form.

According to the present invention, the target cells can be easily separated using the centrifugal force and dielectrophoresis.

Consequently, a fluid and target cells are ejected to the outside of a rotation disk due to a centrifugal force of the rotation disk. In addition, the target cells are positioned adjacent to the rotation disk, and the fluid is positioned at an edge of a lower plate of high electric field due to dielectrophoresis. According to rotation of the rotation disk, pivot arms open second fluid flow paths, and collect the target cells adjacent to the rotation disk. Accordingly, the target cells can be easily separated. In addition, if there are a plurality of storage portions, the target cells may be simultaneously obtained at several places, resulting in improvement of cell separation efficiency.

While exemplary embodiments of the present invention have been shown and described, it will be appreciated by those skilled in the art that various changes can be made to the described exemplary embodiments without departing from the spirit and scope of the invention defined by the claims and their equivalents.

The invention claimed is:

1. An apparatus for separating a cell, comprising:
    a lower plate;
    microelectrode parts on the lower plate for generating a dielectrophoresis electric field;
    a rotation disk rotatably installed on the lower plate configured to eject by centrifugal force target cells stored inside a storage portion located on the rotation disk, wherein the electric field can be used to collect the elected target cells; and
    an upper cover placed over the lower plate to make a space for accommodating the rotation disk.

2. The apparatus according to claim 1, wherein the rotation disk includes pivot arms, which selectively pivot in an outer direction of a radius during rotation of the rotation disk to collect the target cells relocated outside the rotation disk.

3. The apparatus according to claim 2, wherein the rotation disk further includes a plurality of fluid flow paths through which the target cells collected by the pivot arms flow inside and another storage portion storing the target cells flowing through the plurality of fluid flow paths.

4. The apparatus according to claim 3, wherein the pivot arms are placed on an outer surface of the rotation disk to block inlets of the plurality of fluid flow paths, and pivot to open the plurality of fluid flow paths during the rotation of the rotation disk.

5. The apparatus according to claim 4, wherein the pivot arms pivot by a centrifugal force generated during the rotation of the rotation disk.

6. The apparatus according to claim 4, wherein the pivot arms are curved and thus have projecting portions from the outer surface of the rotation disk, and pivot under the influence of resistance acting on the projecting portions during the rotation of the rotation disk.

7. The apparatus according to claim 4, wherein the another storage portion is formed at the center of the rotation disk, and connected with the plurality of fluid flow paths.

8. The apparatus according to claim 1, wherein the storage portion is configured so that the target cells can be injected from outside initially, and wherein the rotation disk further includes a fluid flow path from which the target cells stored in the storage portion are ejected to outside during initial driving of the rotation disk.

9. The apparatus according to claim 8, wherein the storage portion is spaced a bit apart from the center of the rotation disk.

10. The apparatus according to claim 1, wherein the microelectrode parts are placed outside the rotation disk, and form an electric field whose strength is weaker toward the center of the rotation disk.

11. The apparatus according to claim 10, wherein the microelectrode parts include first microelectrodes placed under the rotation disk and second microelectrodes placed over the rotation disk, and the first and second microelectrodes are positioned to face each other on the basis of a space for the rotation disk.

12. The apparatus according to claim 11, wherein the first microelectrodes are integrated with the lower plate, and the second microelectrodes are integrated with the upper cover.

* * * * *